United States Patent
Mao et al.

(10) Patent No.: US 8,771,752 B2
(45) Date of Patent: Jul. 8, 2014

(54) COMPOSITION FOR PREVENTING AND TREATING FATTY LIVER

(75) Inventors: Frank Chiahung Mao, Taichung (TW); Wen-Ying Chen, Longjing Township, Taichung County (TW)

(73) Assignee: National Chung Hsing University, Taichung (TW)

( * ) Notice: Subject to any disclaimer, the term of this patent is extended or adjusted under 35 U.S.C. 154(b) by 212 days.

(21) Appl. No.: 13/300,793

(22) Filed: Nov. 21, 2011

(65) Prior Publication Data

US 2012/0064176 A1 Mar. 15, 2012

Related U.S. Application Data

(62) Division of application No. 12/457,996, filed on Jun. 29, 2009, now abandoned.

(30) Foreign Application Priority Data

Jul. 7, 2008 (TW) .............................. 97125541 A

(51) Int. Cl.

| A61K 33/24 | (2006.01) |
|---|---|
| A61K 36/06 | (2006.01) |
| A61K 38/17 | (2006.01) |
| A23L 1/304 | (2006.01) |
| A23L 1/305 | (2006.01) |
| A61K 35/20 | (2006.01) |
| A61K 38/40 | (2006.01) |

(52) U.S. Cl.
CPC ............... *A23L 1/304* (2013.01); *A23L 1/3056* (2013.01); *A61K 33/24* (2013.01); *A61K 35/20* (2013.01); *A61K 36/06* (2013.01); *A61K 38/40* (2013.01); *A61K 2300/00* (2013.01)
USPC .................... 424/655; 424/195.16; 514/21.92

(58) Field of Classification Search
CPC ...... A23L 1/304; A23L 1/3056; A61K 33/24; A61K 35/20; A61K 36/06; A61K 38/40
USPC .................... 424/655, 195.16; 514/8.6, 21.92
See application file for complete search history.

(56) References Cited

U.S. PATENT DOCUMENTS

| 6,379,693 | B1 | 4/2002 | Mao et al. | |
|---|---|---|---|---|
| 6,852,760 | B1 * | 2/2005 | Fine et al. | 514/593 |
| 7,119,110 | B2 * | 10/2006 | Bagchi et al. | 514/356 |
| 7,956,031 | B2 * | 6/2011 | Naidu et al. | 514/2.5 |
| 2008/0268069 | A1 * | 10/2008 | Yae et al. | 424/655 |
| 2010/0285152 | A1 * | 11/2010 | Pilvi et al. | 424/682 |

FOREIGN PATENT DOCUMENTS

| CN | 1473852 A | 2/2004 |
|---|---|---|
| CN | 1736478 A | 2/2006 |
| EP | 1 466 621 A1 | 10/2004 |
| GB | 2 416 693 A | 2/2006 |
| JP | 2007197327 | 8/2007 |
| JP | 2007326800 | 12/2007 |

OTHER PUBLICATIONS

Merck (Fatty Liver, Merck Manuals, (last review/revision Sep. 2007) [Downloaded Feb. 10, 2012] [Retrieved from internet <URL: http://www.merckmanuals.com/home/print/liver_and_gallbladder_disorders/fatty_liver_cirrhosis_and_related_disorders/fatty_liver.html >]), 2 pages.*
USDA (NAS, IOM, Food and Nutrition Board), Dietary Reference Intakes (DRIs): Recommended Daily Allowances and Adequate Intakes,[Retrueved from internet <URL:http://iom.edu/Activities/Nutrition/SummaryDRIs/~/media/Files/Activity%20Files/Nutrition/DRIs/RDA%20and%20AIs_Vitamin%20and%20Elements.pdf >], (updated regarding Chromium, 2001), 3 pages.*
Chen et al., Chromium Supplementation enhances insulin signalling in skeletal muscle of obese KK/HIJ diabetic mice, Diabetes, Obesity and Metabolism (Apr. 2009) 11: 293-303, teaches 8 mcg/kg body wt/day trivalent chromium formulated with milk powder but does not give a concentration of lactoferrin. (p. 294, col. 2, Animals and Diets).*
Chen et al., Chromium attenuates hepatic damage in a rat model of chronic cholestatsis, Life Sciences (Apr. 2009), 84: 606-614, also teaches 8 mcg/kg body wt/day trivalent chromium in milk powder, but does not teach a concentration of lactoferrin. (p. 607, col. 1, Animals).*
Chen et al., Lactoferrin Concentration in Mestatic Goat Milk, The Journal of Veterinary Medical Science (2004), Abs. [Retrieved from internet <URL: https://www.jstage.jst.go.jp/browse/jvms/66/5_contents/>], teaches varying concentrations of lactoferrin in goat's milk. (Abs.).*

* cited by examiner

*Primary Examiner* — Jason Sims
*Assistant Examiner* — Miriam A Levin
(74) *Attorney, Agent, or Firm* — Bacon & Thomas, PLLC

(57) ABSTRACT

A composition for preventing and treating fatty liver is disclosed. The composition includes a lactoferrin and a trivalent chromium compound. The trivalent chromium compound of the present invention is selected from the group consisting of chromium (III) chloride hexahydrate, chromium (III) chloride, chromium (III) acetate, chromium (III) sulfate, chromium picolinate, chromium nicotinate, chromium GTF, chromium yeast extract, other inorganic salts of trivalent chromium, other organic salts of trivalent chromium, and combinations thereof. The composition of the present invention can provide a beneficial effect in preventing and treating fatty liver by effectively reducing multiple risk factors of fatty liver disease.

11 Claims, No Drawings

COMPOSITION FOR PREVENTING AND TREATING FATTY LIVER

CROSS REFERENCE TO THE RELATED APPLICATION

This is a divisional of U.S. application Ser. No. 12/457,996, filed on Jun. 29, 2009, which claims priority to Taiwanese Application No. 097125541, filed on Jul. 7, 2008, the entire contents of which are incorporated by reference herein.

BACKGROUND OF THE INVENTION

1. Field of the Invention

The present invention relates to a composition for preventing and treating fatty liver and, more particularly, to a composition containing trivalent chromium lactoferrin, which can prevent and treat fatty liver.

2. Description of Related Art

Owing to the development in economics, populations suffered from fatty liver disease have gradually increased. Fatty liver disease is now recognized as the most common liver disease in the world. Moreover, fatty liver disease may progress to advanced fibrosis, cirrhosis and hepatocellular carcinoma and might lead to serious public health problems. Therefore, it is really important for the modern people to study how to prevent and control the fatty liver.

The liver plays a central role in lipid metabolism, importing serum free fatty acids and manufacturing, storing and exporting lipids and lipoproteins. However, the metabolic abnormalities may impair hepatic lipid export, lead to hepatic triglyceride accumulation, and induce the fatty liver disease. Moreover, the fatty liver, which is easily attacked by adipocytokines and oxidative stress, results in the hepatocellular inflammation and fibrosis, and exacerbates disease progression.

The fatty liver disease is a complex metabolic disease. In clinical, the fatty liver only show that fat accumulates in the liver cells and usually dose not damage the liver. However, patients suffered from the fatty liver disease generally are associated with insulin resistance, including glucose intolerance, obesity, hyperglycemia, and hyperlipiemia. Several studies have reported that obesity, diabetes mellitus, hyperlipidemia, insulin resistance, and oxidative stress are major risk factors of the fatty liver disease. Therefore, the treatment of fatty liver is related to improve these risk factors of fatty liver. Many drugs are now being studied for potential medical therapy, including (1) drugs for treating insulin resistance, such as meformin, troglitazone, and rosiglitazone, (2) lipid-lowering medications, such as clofibrate and gemfibrozil, (3) liver protective drugs, such as ursodeoxycholic acid, and (4) antioxidants, such as vitamin E and betaine. However, the therapeutic effect of these drugs on the fatty liver is limited. To date, there is no proven effective therapies available for the prevention and control of fatty liver disease.

SUMMARY OF THE INVENTION

The object of the present invention is to provide a composition for effectively reducing risk factors of fatty liver disease, improving liver function, and preventing and treating fatty liver disease.

To achieve the object, the present invention provides a composition for preventing and treating fatty liver disease, including: a lactoferrin and a trivalent chromium compound. In addition, the present invention further provides a method for preventing and treating fatty liver, including administrating an effective amount of the above-mentioned composition to the acceptor.

The lactoferrin used in the present invention is not particularly restricted, and can come from cow lactoferrin, goat lactoferrin, unpurified cow milk, unpurified goat milk or a combination thereof. Because lactoferrin mainly exists in the whey of the milk, the lactoferrin of the present invention can also be completely or partly replaced with whey protein products or buttermilk powder.

The trivalent chromium compound used in the present invention is not particularly restricted, and can come from inorganic salts of trivalent chromium, organic salts of trivalent chromium or a combination thereof.

The inorganic salts of trivalent chromium include, for example, chromium (III) chloride hexahydrate, chromium (III) chloride and chromium (III) sulfate. The organic salts of trivalent chromium include, for example, chromium (III) acetate, chromium picolinate, chromium nicotinate, amino acid chelated chromium, chromium GTF, chromium yeast extract (such as chromium brewer's yeast extract), and chromium yeast.

Preferably, the trivalent chromium compound is selected from the group consisting of chromium (III) chloride hexahydrate, chromium (III) chloride, chromium (III) acetate, chromium (III) sulfate, chromium picolinate, chromium nicotinate, chromium GTF, chromium yeast extract and a combination thereof.

In general, the ratio of lactoferrin to the trivalent chromium compound in the composition of the present invention is not particularly restricted.

The composition of the present invention can be used to form a medicament. Also, it can be added into a dairy product, and thereby form a dairy product containing trivalent chromium compound and lactoferrin, i.e., form a food or nutriment. The dairy product can be selected from the group consisting of the fresh milk of mammals, long-life milk, concentrated milk, cheese and milk powder.

In the composition of the present invention, the lactoferrin is a glycoprotein that is capable of combining with metal ions. Each lactoferrin molecule can be combined with two trivalent chromium ions and form a trivalent chromium lactoferrin complex. In comparison to the low absorption rate of inorganic chromium and organic chromium (the absorption rate of inorganic chromium only ranges from 0.4% to 3%), the trivalent chromium-lactoferrin complex in the composition of the present invention can be more efficiently absorbed and utilized by the human body.

Therefore, the composition of the present invention can be taken by the high-risk population and patients for fatty live disease. Taking the composition of trivalent chromium and lactoferrin in the present invention, not only can replenish the organic chromium efficiently, but also can reduce the risk factors of fatty liver disease, such as obesity, hyperglycemia, hyperlipidemia, insulin resistance, and oxidantive stress, and then enhance the normal metabolism of fat, carbohydrates, and protein. Therefore, taking the composition of trivalent chromium and lactoferrin in the present invention can effectively prevent and treat fatty liver.

Other objects, advantages, and novel features of the invention will become more apparent from the following detailed description when taken in conjunction with the accompanying drawings.

BRIEF DESCRIPTION OF THE DRAWINGS

None

DETAILED DESCRIPTION OF THE PREFERRED EMBODIMENT

The composition of the present invention can be formed by mixing the powder of lactoferrin with the powder of trivalent chromium compound. Moreover, water can also be added into the mixture of lactoferrin and the trivalent chromium compound to form a mixed solution. The mixed solution can be heated properly so that the mixing can be done adequately. The heating temperature ranges around 37° C. to 95° C., and preferably ranges from 50° C. to 80° C. The well-mixed solution can be then spray-dried to form the composition containing trivalent chromium lactoferrin of the present invention.

The raw material of the trivalent chromium compound used in the present invention can be inorganic salts or organic salts, such as chromium (III) chloride hexahydrate, chromium (III) chloride, chromium (III) acetate, chromium (III) sulfate, chromium picolinate, chromium nicotinate, chromium GTF, chromium yeast extract or chromium yeast.

Lactoferrin could come from the solution or dry powder of lactoferrin, unpurified cow milk or unpurified goat milk. Because lactoferrin mainly exists in the whey of the milk, the present invention can also use an unpurified whey protein product or buttermilk powder.

The following detailed description is given by way of example and not intended to limit the invention solely to the embodiments described herein.

EXAMPLE 1

Lactoferrin powder (3 g) and chromium (III) chloride hexahydrate (0.5 g) are added to pure water (1 liter), followed by stirring to form a solution. The solution is well-mixed, spray-dried, and then mixed with buttermilk powder (196 g) and whey protein (100 g) to form the composition containing trivalent chromium lactoferrin of the present invention.

EXAMPLE 2

Lactoferrin powder (60 g), whey protein (400 g) and chromium (III) chloride hexahydrate (1 g) are added to pure water (2 liter) and heated to around 50° C., followed by stirring to form a solution. The solution is mixed with buttermilk powder (200 kg) and spray-dried to form the composition containing trivalent chromium lactoferrin of the present invention.

EXAMPLE 3

Lactoferrin powder (3 g), whey protein (30 g) and chromium (III) chloride hexahydrate (154.5 g) are added to pure water (1 liter) and heated to around 50° C., followed by stirring to form a solution. The solution is mixed with buttermilk powder (50 kg) and whey protein (25 kg) and spray-dried to form the composition containing trivalent chromium lactoferrin of the present invention.

TEXT EXAMPLE 1

The chromium dairy product obtained from Example 1 is mixed into a mouse diet (Modified LabDiet w/35.5% Lard, PMI® Richmond, Ind., USA). At 10 weeks of age, glucose tolerance test (OTT) are performed after an overnight fast. According to the results of GTT, the C57BL/6JNarl mice are randomly divided into two groups. The experimental group is supplemented with a chromium dairy product (0.24 g/kg BW/day, containing trivalent chromium 80 mcg/kg BW/day), and the control group is not supplemented. After 5 weeks of chromium dairy product supplementation, the C57BL/6JNarl mice are fasted overnight and GTT is performed again. The changes of blood glucose during the GTT are shown in Table 1. At the beginning of the experiment, the levels of blood glucose are similar in two groups. However, the levels of blood glucose at 30 and 180 minutes are significantly reduced in the experimental group after receiving a chromium dairy product supplementation for 5 weeks. These data suggests that glucose tolerance is significantly improved in the experimental group.

TABLE 1

| Baseline | Control group (N = 6) | Experimental group (N = 6) |
|---|---|---|
| 0 min | 115 ± 19 | 122 ± 31 |
| 30 min | 283 ± 25 | 270 ± 53 |
| 60 min | 237 ± 52 | 244 ± 53 |
| 120 min | 170 ± 37 | 167 ± 20 |
| 180 min | 133 ± 19 | 139 ± 14 |
| After supplement for 5 weeks | Control group (N = 6) | Expeimental group (N = 6) |
| 0 min | 128 ± 13 | 115 ± 11 |
| 30 min | 329 ± 15 | 274 ± 29** |
| 60 min | 274 ± 34 | 247 ± 16 |
| 120 min | 196 ± 25 | 171 ± 22 |
| 180 min | 161 ± 8 | 143 ± 12* |

*$p < 0.05$, significant difference vs. control group.
**$p < 0.01$, significant difference vs. control group.
N means the number of mice.

TEST EXAMPLE 2

The chromium dairy product obtained from Example 1 is mixed into a mouse diet (Modified LabDiet w/35.5% Lard, PMI® Richmond, Ind., USA). At 10 weeks of age, glucose tolerance test (GTT) are performed after an overnight fast. According to the results of GTT, the C57BL/6JNarl mice are randomly divided into two groups. The experimental group is supplemented with a chromium dairy product (0.24 g/kg BW/day, containing trivalent chromium 80 mcg/kg BW/day), and the control group is not supplemented. After 8 weeks of chromium dairy product supplementation, the C57BL/6JNarl mice are fasted overnight and the body weights, the levels of serum triglycerides, serum glutamic oxaloacetic transaminase (SGOT) and serum glutamic pyruvic transaminase (SGPT) are recorded. The results are shown below in Table 2. As a result, the body weight and the levels of serum triglyceride and SGPT are significantly reduced in C57BL/6JNarl mice supplemented with a chromium dairy product compared to those in the control C57BL/6JNarl mice. These results show that body weight, blood lipid and liver function are significantly improved in the experimental group. Therefore, these results suggest that the chromium dairy product is beneficial in preventing and treating fatty liver.

TABLE 2

|  | Control group (N = 6) | Experimental group (N = 6) |
|---|---|---|
| Body weight (g) | 28.5 ± 1.2 | 26.7 ± 1.2* |
| Triglycerides (mg/dl) | 193 ± 22 | 164 ± 18* |
| SGOT (U/l) | 368 ± 47 | 267 ± 121 |
| SGPT (U/l) | 53 ± 13 | 29 ± 7* |

*$p < 0.05$, significant difference vs. control group.
N means the number of mice.

TEST EXAMPLE 3

The chromium dairy product obtained from Example 1 is mixed into a mouse diet (Modified LabDiet w/35.5% Lard, PMI® Richmond, Ind., USA). At 10 weeks of age, glucose tolerance test (OTT) are performed after an overnight fast. According to the results of OTT, the C57BL/6JNarl mice are randomly divided into two groups. The experimental group is supplemented with a chromium dairy product (0.24 g/kg BW/day, containing trivalent chromium 80 mcg/kg BW/day), and the control group is not supplemented. After 8 weeks of chromium dairy product supplementation, the C57BL/6JNarl mice are sacrificed and their livers are harvested. Then, the changes in the activities of hepatic antioxidative enzymes are analyzed. As shown in Table 3, the levels of hepatic vitamin E and catalase are significantly increased in C57BL/6JNarl mice supplemented with a chromium dairy product compared to that in the control C57BL/6JNarl mice. Therefore, these results suggest that the chromium dairy product supplementation improves antioxidative ability in the experimental group.

TABLE 3

|  | Control group (N = 6) | Experimental group (N = 6) |
| --- | --- | --- |
| Vitamin E (nmol/mcg protein) | 62.4 ± 3.9 | 70.6 ± 6.5* |
| Catalase activity (nmol/min/ml/mcg protein) | 3.5 ± 1.0 | 5.7 ± 0.6** |

*p < 0.05, significant difference vs. control group.
**p < 0.01, significant difference vs. control group.
N means the number of mice.

TEST EXAMPLE 4

The chromium dairy product obtained from Example 1 is mixed into a mouse diet (Modified LabDiet w/35.5% Lard, PMI® Richmond, Ind., USA). At 10 weeks of age, glucose tolerance test (GTT) are performed after an overnight fast. According to the results of GTT, the C57BL/6JNarl mice are randomly divided into two groups. The experimental group is supplemented with a chromium dairy product (0.24 g/kg BW/day, containing trivalent chromium 80 mcg/kg BW/day), and the control group is not supplemented. After 8 weeks of chromium dairy product supplementation, the C57BL/6JNarl mice are sacrificed and their livers are harvested. Then, the level of hepatic triglycerides is analyzed. As shown in Table 4, the level of hepatic triglycerides is significantly reduced in C57BL/6JNarl mice supplemented with a chromium dairy product compared to that in the control C57BL/6JNarl mice. This result indicates that the chromium dairy product supplementation improves fatty liver in the experimental group.

TABLE 4

|  | Control group (N = 6) | Experimental group (N = 6) |
| --- | --- | --- |
| Hepatic triglycerides (μ mol/g liver) | 36.7 ± 4.4 | 25.6 ± 1.8*** |

***p < 0.001, significant difference vs. control group.
N means the number of mice.

TEST EXAMPLE 5

The chromium dairy product obtained from Example 1 is mixed into a mouse diet (Modified LabDiet w/35.5% Lard, PMI® Richmond, Ind., USA). At 10 weeks of age, glucose tolerance test (GTT) are performed after an overnight fast. According to the results of GTT, the C57BL/6JNarl mice are randomly divided into two groups. The experimental group is supplemented with a chromium dairy product (0.24 g/kg BW/day, containing trivalent chromium 80 mcg/kg BW/day), and the control group is not supplemented. After 8 weeks of chromium dairy product supplementation, the C57BL/6JNarl mice are sacrificed and their livers are harvested. Then, the livers are fixed with 10% neutral formalin solution and embedded with paraffin wax. Serial sections (10 μm thick) are cut from each specimen and stained with hematoxylin and eosin (H & E). Coded histologic slides are examined and scored by an experienced pathologist, blind for the supplement. The scores are as follows:
score 0: no visible fat;
score 1: <5% of liver surface infiltrated by fat
score 2: 5% to 25% of liver surface infiltrated by fat;
score 3: 25% to 50% of liver surface infiltrated by fat; and
score 4: >50% of liver surface infiltrated by fat.

As shown in Table 5, in mice the score decrease from a mean of 3.5±0.76 in the control group to 1.5±0.96 in the experimental group. These results suggest that chromium dairy product supplementation improves fatty liver in the experimental mice.

TABLE 5

| Score | Control group (N = 6) | Experimental group (N = 6) |
| --- | --- | --- |
| 0 | — | 1 |
| 1 | — | 2 |
| 2 | 1 | 2 |
| 3 | 1 | 1 |
| 4 | 4 | — |
| Mean ± SD | 3.5 ± 0.76 | 1.5 ± 0.96** |

**p < 0.01, significant difference vs. control group.
N means the number of mice.

TEST EXAMPLE 6

The chromium dairy product obtained from Example 2 is mixed into a mouse diet (high-fat Rodent TestDiet, PMI International Inc., MO, USA; 67% of calories provided by fat). The experimental group is supplemented with a chromium dairy product (8 g/kg BW/day, containing trivalent chromium 80 mcg/kg BW/day), and the control group is not supplemented. The KK/HlJ mice aged 8 weeks are fed for 8 weeks, fasted overnight and then sacrificed. Moreover, the bloods are collected and their livers are harvested. Then, the levels of serum triglycerides, serum cholesterol, SGOT and SGPT, and TBARs and triglycerides in liver are analyzed. As a result, the levels of triglycerides, cholesterol, SGOT and SGPT are significantly reduced in serum of KK/HlJ mice supplemented with a chromium dairy product compared to that of the control KK/HlJ mice. Moreover, the hepatic TBARs and triglycerides are significantly reduced in the experimental group. These results show that dyslipidemia, liver function, and fatty liver are significantly improved and a lipid peroxidation product TBARs is significantly reduced in the experimental group. Therefore, these results suggest that the chromium dairy product is beneficial in preventing and treating fatty liver.

TABLE 6

|  | Control group (N = 7) | Experimental group (N = 7) |
| --- | --- | --- |
| triglycerides (mg/dl) | 119 ± 16 | 93 ± 15* |
| Cholesterol (mg/dl) | 165 ± 19 | 125 ± 14** |
| AST (U/l) | 306 ± 44 | 239 ± 37* |

TABLE 6-continued

|  | Control group (N = 7) | Experimental group (N = 7) |
|---|---|---|
| ALT (U/l) | 31 ± 9 | 11 ± 4*** |
| Hepatic TBARs (nmol/mg protein) | 49 ± 21.4 | 12.5 ± 11.1** |
| Hepatic triglycerides (μ mol/g liver) | 118 ± 33 | 78 ± 24*** |

**p < 0.05, significant difference vs. control group.
**p < 0.01, significant difference vs. control group.
***p < 0.001, significant difference vs. control group.
N means the number of mice.

From Table 1 to Table 6, it is proven that the fatty liver disease can be effectively improved after taking the dairy product containing the composition of the present invention. The dose level of 80 g/kg/day $Cr^{+3}$ in the composition of lactoferrin and trivalent chromium for mice can provide a beneficial effect in preventing and controlling fatty liver disease. Therefore, according to the metabolic rate ratio, the dose level of $Cr^{+3}$ in the composition of lactoferrin and trivalent chromium for human to provide a beneficial effect in preventing and controlling fatty liver disease is calculated at around 8 μg/kg/day (the metabolic rate ratio of mouse to human is 10).

TEST EXAMPLE 7

Male C57BL/6JNarl mice (n=70) fed with high fat diet (high-fat Rodent TestDiet, PMI International Inc., MO, USA; 67% of calories provided by fat), age 8 weeks, are randomly divided into the control group, the low-dose lactoferrin group (NZMP lactoferrin, New Zealand, 40 mg/kg BW/day), the high-dose lactoferrin group (80 mg/kg BW/day), the low-dose chromium group ($CrCl_3 \cdot 6H_2O$, Sigma, $Cr^{+3}$ 40 μg/kg BW/day), the high dose chromium group ($Cr^{+3}$ 80 μg/kg BW/day), the low-dose lactoferrin+chromium group (lactoferrin 40 mg/kg BW/day+$Cr^{+3}$ 40 μg/kg BW/day), and the high-dose lactoferrin+chromium group (lactoferrin 80 mg/kg BW/day+$Cr^{+3}$ 80 μg/kg BW/day) (10 mice in each group). After supplementation for 7 weeks, the C57BL/6JNarl mice are sacrificed and their livers are harvested. Then, the level of hepatic triglycerides is analyzed. As shown in Table 7, the level of hepatic triglycerides is significantly reduced in C57BL/6JNarl mice supplemented with high dose lactoferrin+chromium compared to that in the control C57BL/6JNarl mice. However, no significant difference between the other groups is found. Therefore, these results suggest that the supplementation with chromium plus lactoferrin is significant better than that supplementation with only lactoferrin or chromium.

TABLE 7

|  |  | Hepatic triglycerides (μ mol/g liver) |
|---|---|---|
|  | Control | 21.9 ± 63 |
| Lactoferrin | Low-dose | 18.4 ± 6.0 |
|  | High-dose | 18.1 ± 7.2 |
| chromium | Low-dose | 18.4 ± 8.1 |
|  | High-dose | 19.0 ± 5.7 |
| Lactoferrin + Chromium | Low-dose | 18.4 ± 7.4 |
|  | High-dose | 14.0 ± 4.6** |

**P < 0.01, significant difference vs. control group.

In conclusion, the composition of the present invention can be taken by the high-risk population and patients for fatty live disease. Taking the composition of trivalent chromium and lactoferrin in the present invention can reduce the risk factors of fatty liver disease, such as obesity, hyperglycemia, dyslipidemia, insulin resistance, and oxidantive stress, enhance the hepatic antioxidative ability, improve liver function, increase the hepatic lipid metabolism, and alleviate the fatty liver disease.

Although the present invention has been explained in relation to its preferred embodiment, it is to be understood that many other possible modifications and variations can be made without departing from the scope of the invention as hereinafter claimed.

What is claimed is:

1. A method for improving liver function, wherein the method comprises administering to a subject in need thereof an effective amount of a composition comprising:
    (a) a lactoferrin; and
    (b) a trivalent chromium compound; wherein the trivalent chromium compound is selected from the group consisting of chromium (III) chloride hexahydrate, chromium (III) chloride, chromium (III) acetate, chromium (III) sulfate, chromium picolinate, chromium nicotinate, chromium GTF, chromium yeast extract, other inorganic salts of trivalent chromium, other organic salts of trivalent chromium, and combinations thereof,
    wherein said effective amount comprises 8 mg/kg body weight (BW)/day of lactoferrin and 8 μg/kg BW/day of trivalent chromium, and
    wherein the subject is a human.

2. The method of claim 1, wherein the composition is used to reduce serum glutamic oxaloacetic transaminase (SGOT) and serum glutamic pyruvic transaminase (SGPT).

3. The method of claim 1, wherein the lactoferrin comes from unpurified milk or whey protein.

4. The method of claim 1, wherein the lactoferrin is selected from the group consisting of cow lactoferrin, goat lactoferrin, unpurified cow milk, unpurified goat milk, and combinations thereof.

5. The method of claim 1, wherein the trivalent chromium compound is selected from the group consisting of chromium (III) chloride hexahydrate, chromium (III) chloride, chromium (III) acetate, chromium (III) sulfate, chromium picolinate, chromium nicotinate, chromium GTF, chromium yeast extract, and combinations thereof.

6. The method of claim 1, wherein the composition serves as an additive of a dairy product, which is selected from the group consisting of fresh milk of mammals, long-life milk, concentrated milk, fermented milk, cheese, and milk powder.

7. A method for treating fatty liver, wherein the method comprises administering to a subject in need thereof an effective amount of a composition comprising:
    (a) a lactoferrin; and
    (b) a trivalent chromium compound; wherein the trivalent chromium compound is selected from the group consisting of chromium (III) chloride hexahydrate, chromium (III) chloride, chromium (III) acetate, chromium (III) sulfate, chromium picolinate, chromium nicotinate, chromium glucose tolerance factor (GTF), chromium yeast extract, other inorganic salts of trivalent chromium, other organic salts of trivalent chromium, and combinations thereof,
    wherein said effective amount comprises 8 mg/kg body weight (BW)/day of lactoferrin and 8 μg/kg BW/day of trivalent chromium, and
    wherein the subject is a human.

8. The method of claim 7, wherein the lactoferrin comes from unpurified milk or whey protein.

9. The method of claim 7, wherein the lactoferrin is selected from the group consisting of cow lactoferrin, goat lactoferrin, unpurified cow milk, unpurified goat milk, and combinations thereof.

10. The method of claim 7, wherein the trivalent chromium compound is selected from the group consisting of chromium (III) chloride hexahydrate, chromium (III) chloride, chromium (III) acetate, chromium (III) sulfate, chromium picolinate, chromium nicotinate, chromium GTF, chromium yeast extract, and combinations thereof.

11. The method of claim 7, wherein the composition serves as an additive of a dairy product, which is selected from the group consisting of fresh milk of mammals, long-life milk, concentrated milk, fermented milk, cheese, and milk powder.

* * * * *